United States Patent
Kobayashi et al.

(10) Patent No.: US 12,108,976 B2
(45) Date of Patent: Oct. 8, 2024

(54) TREATMENT TOOL

(71) Applicant: OLYMPUS CORPORATION, Tokyo (JP)

(72) Inventors: Marina Kobayashi, Sagamihara (JP); Yoshinori Homma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 742 days.

(21) Appl. No.: 17/232,629

(22) Filed: Apr. 16, 2021

(65) Prior Publication Data

US 2021/0228265 A1 Jul. 29, 2021

Related U.S. Application Data

(63) Continuation of application No. PCT/JP2018/039208, filed on Oct. 22, 2018.

(51) Int. Cl.
*A61B 18/14* (2006.01)
*A61B 18/00* (2006.01)

(52) U.S. Cl.
CPC ............ *A61B 18/1445* (2013.01); *A61B 2018/00202* (2013.01); *A61B 2018/00994* (2013.01)

(58) Field of Classification Search
CPC ............ A61B 18/1442; A61B 18/1445; A61B 18/1447; A61B 2018/145; A61B 2018/1452; A61B 2018/1455; A61B 2018/1457; A61B 17/2804; A61B 17/29; A61B 2090/035; A61B 17/320092; A61B 17/320094; A61B 2017/2926; A61B 2017/2947

See application file for complete search history.

(56) References Cited

U.S. PATENT DOCUMENTS 5,827,263 A * 10/1998 Furnish .............. A61B 17/2909
606/1
11,801,086 B2   10/2023 Morisaki
(Continued)

FOREIGN PATENT DOCUMENTS

CN    102596080 A    7/2012
CN    105120784 A    12/2015
(Continued)

OTHER PUBLICATIONS

Jan. 8, 2019 Search Report issued in International Patent Application No. PCT/JP2018/039208.
(Continued)

*Primary Examiner* — Linda C Dvorak
*Assistant Examiner* — Davina E. Lee
(74) *Attorney, Agent, or Firm* — Oliff PLC

(57) ABSTRACT

A treatment tool includes: an elongated shaft; a probe that protrudes from a distal end of the shaft; a movable jaw that is mounted in a rotatable manner; and a swing arm that is mounted on the movable jaw. The swing arm is capable of gripping living tissue with the probe and swinging with respect to the movable jaw. The movable jaw includes a first regulating surface that can contact a proximal end portion of the swing arm to regulate swinging of the swing arm in one direction, and a second regulating surface that can contact another region in the proximal end portion of the swing arm to regulate swinging of the swing arm in another direction.

15 Claims, 8 Drawing Sheets

(56) References Cited

U.S. PATENT DOCUMENTS

| | | |
|---|---|---|
| 2004/0186463 A1 | 9/2004 | Murakami et al. |
| 2010/0057084 A1 | 3/2010 | Hanna |
| 2011/0184404 A1* | 7/2011 | Walberg ............ A61B 18/1445 |
| | | 606/41 |
| 2015/0327918 A1 | 11/2015 | Sobajima et al. |
| 2015/0374428 A1 | 12/2015 | Sobajima et al. |
| 2017/0000556 A1* | 1/2017 | Morisaki ............ A61B 18/1206 |

FOREIGN PATENT DOCUMENTS

| | | |
|---|---|---|
| WO | 2004/012615 A1 | 2/2004 |
| WO | 2014/148280 A1 | 9/2014 |
| WO | 2014/148281 A1 | 9/2014 |
| WO | 2018/011920 A1 | 1/2018 |

OTHER PUBLICATIONS

Sep. 28, 2023 Office Action issued in Chinese Patent Application No. 201880098901.5.

Apr. 25, 2024 Office Action issued in Chinese Patent Application No. 201880098901.5.

\* cited by examiner

TREATMENT TOOL

CROSS-REFERENCE TO RELATED APPLICATION

This application is a continuation of International Application No. PCT/JP2018/039208, filed on Oct. 22, 2018, the entire contents of which are incorporated herein by reference.

BACKGROUND

1. Technical Field

The disclosure relates to a treatment tool.

2. Related Art

In the related art, a treatment tool in which a piezoelectric unit that applies ultrasound energy (ultrasound vibration) to living tissue is arranged, and which performs treatment (suture (or anastomosis), dissection, and the like) on the living tissue by applying the ultrasound vibration has been known.

For instance, the treatment tool can include two gripper members for gripping living tissue. In the treatment tool, the two gripper members constitute an end effector. A swinging member that swings about a predetermined axis may be arranged on one of the gripper members. The swinging member includes a distal-end-side contact surface that comes close to a distal end portion of the gripper member, and a proximal-end-side contact surface that comes close to a proximal end portion of the gripper member. A swing range may be regulated by contact between the distal-end-side contact surface or the proximal-end-side contact surface of the swinging member and the gripper member.

SUMMARY

In some embodiments, a treatment tool includes: an elongated shaft; a probe that protrudes from a distal end of the shaft; a movable jaw that is mounted in a rotatable manner; and a swing arm that is mounted on the movable jaw. The swing arm is capable of gripping living tissue with the probe and swinging with respect to the movable jaw. The movable jaw includes a first regulating surface that can come into contact with a proximal end portion of the swing arm to regulate swinging of the swing arm in one direction, and a second regulating surface that can come into contact with a different region in the proximal end portion of the swing arm to regulate swinging of the swing arm in another direction.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of a treatment tool according to the disclosure will be described below with reference to the drawings. The disclosure is not limited by the embodiments below. Furthermore, in describing the drawings, the same components are denoted by the same reference symbols.

Figure 1:
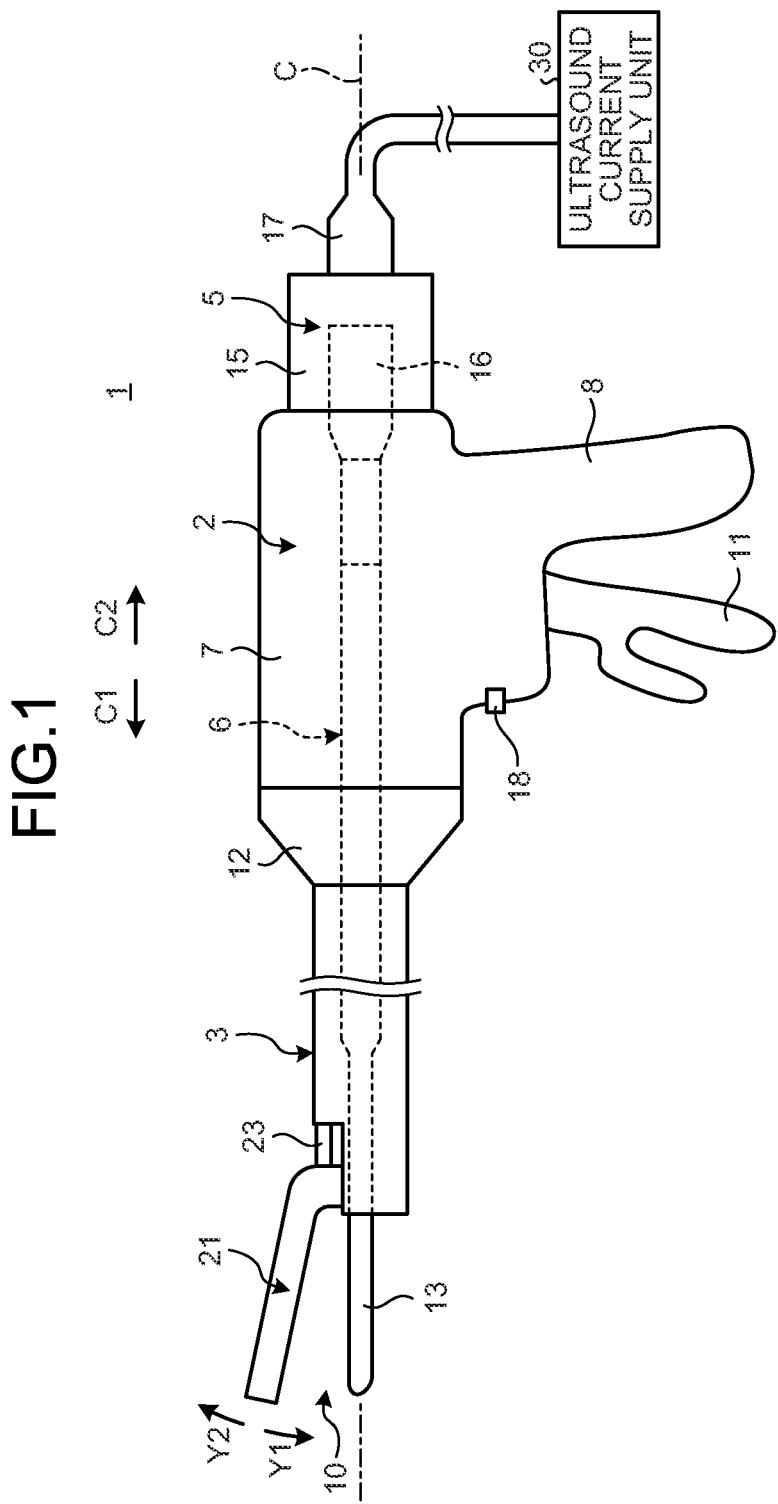
FIG. 1 is a schematic diagram illustrating an exemplary treatment tool according to an embodiment of the disclosure.

FIG. 1 is a schematic diagram illustrating a treatment tool according to one embodiment of the disclosure. A treatment tool 1 includes a housing 2, a shaft 3, a transducer unit 5, and a rod member (probe) 6. The shaft 3 includes a longitudinal axis C as a central axis. Here, one side in a direction along the longitudinal axis C is a distal end side (an arrow C1 side), and an opposite side of the distal end side is a proximal end side (an arrow C2 side).

The housing 2 is connected to a proximal end side of the shaft 3. The housing 2 includes a housing main body 7 that extends in the longitudinal axis C, and a grip 8 that extends from the housing main body 7 in a direction crossing the longitudinal axis C. Further, a handle 11 is mounted on the housing 2 in a rotatable manner. The grip 8 and the handle 11 are portions held by an operator by hand. The handle 11 rotates about a mounting position on the housing 2 with respect to the housing 2, so that the handle 11 comes close to or away from the grip 8. Meanwhile, in the present embodiment, the handle 11 is located on the distal end side relative to the grip 8 and a moving direction of the handle 11 with respect to the grip 8 is approximately parallel to the longitudinal axis C, but embodiments are not limited to this example. For example, the handle 11 may be arranged on the proximal end side relative to the grip 8, or the moving direction of the handle 11 with respect to the grip 8 may be approximately perpendicular to the longitudinal axis C.

Furthermore, in the present embodiment, a rotation member (rotation knob) 12 is mounted on the housing main body 7 from the distal end side. The shaft 3 is inserted into the rotation member 12 from the distal end side. The shaft 3 is fixed to the rotation member 12, and is rotatable together with the rotation member 12 about the longitudinal axis C with respect to the housing 2.

The transducer unit 5 includes a transducer case 15 and an ultrasound transducer 16 (ultrasound vibrator). The transducer case 15 is mounted on the housing main body 7 from the proximal end side. Further, one end of a cable 17 is connected to the transducer case 15. The other end of the cable 17 is removably connected to an ultrasound current supply unit 30 that performs energy control. The ultrasound transducer 16 includes a piezoelectric element (not illustrated) that generates ultrasound vibration, and is arranged inside the transducer case 15. The ultrasound transducer 16 is extended along the longitudinal axis C. The ultrasound transducer 16 is connected to the rod member 6 from the proximal end side inside the housing main body 7. Meanwhile, one end of the cable 17 may be connected to the housing 2.

The rod member 6 transmits ultrasound vibration. The rod member 6 is extended to the distal end side along the longitudinal axis C from the inside of the housing 2 through the inside of the shaft 3. A treatment unit (rod treatment unit) 13 is arranged on a distal end portion of the rod member 6. The rod member 6 is inserted into the shaft 3 and arranged such that the treatment unit 13 protrudes from a distal end of the shaft 3. The rod member 6 is made of, for example, a titanium alloy or a stainless alloy. The rod member 6 corresponds to a gripper member.

Furthermore, an operation button 18 is mounted on the housing 2. The operation button 18, when pressed by an operator, inputs an operation instruction to cause the ultrasound current supply unit 30 to output electrical energy. If an instruction is input by the operation button 18, the ultrasound current supply unit 30 supplies, as electrical energy, alternating-current power at a predetermined frequency to the ultrasound transducer 16 via electrical wiring (not illustrated) or the like inside the cable 17. With the supply of the electrical energy, the ultrasound transducer 16 (piezoelectric element) converts the electrical energy to ultrasound vibration and generates the ultrasound vibration. The ultrasound vibration generated by the ultrasound transducer 16 is transmitted from the proximal end side to the distal end side in the rod member 6. Then, the ultrasound vibration is transmitted to the treatment unit 13 of the rod member 6. By the transmission of the ultrasound vibration, the ultrasound transducer 16 and the rod member 6 vibrate at certain frequencies in a predetermined frequency range. In this case, the vibration directions of the rod member 6 and the ultrasound transducer 16 are approximately parallel to the longitudinal axis C. Meanwhile, it may be possible to input an operation instruction by a foot switch or the like separated from the treatment tool 1, instead of the operation button 18.

A gripper piece 21 is mounted on a distal end portion of the shaft 3 in a rotatable manner. A movable member 23 is extended along the longitudinal axis C inside the shaft 3. A distal end portion of the movable member 23 is connected to the gripper piece 21. The movable member 23 is extended to the inside of the housing 2. The handle 11 is connected to the movable member 23 inside the housing main body 7. The handle 11 comes close to or away from the grip 8, so that the movable member 23 moves along the longitudinal axis C. By the movement of the movable member 23, a driving force acts from the movable member 23 to the gripper piece 21, so that the gripper piece 21 rotates about a mounting position on the shaft 3. Accordingly, the gripper piece 21 is opened or closed with respect to the treatment unit 13. By closing a gap between the gripper piece 21 and the treatment unit 13, a treatment target, such as living tissue, is gripped between the gripper piece 21 and the treatment unit 13. Meanwhile, an opening direction (a direction of an arrow Y2) and a closing direction (a direction of an arrow Y1) of the gripper piece 21 cross the longitudinal axis C. Further, in a state in which the gap between the gripper piece 21 and the treatment unit 13 is closed, a longitudinal direction of the gripper piece 21 is approximately parallel to the longitudinal axis C of the shaft 3. Here, the movable member 23 may be extended to the outside of the shaft 3. If the movable member 23 is arranged outside of the shaft 3, for example, the shaft 3 is extended inside the movable member 23.

In the present embodiment, the treatment unit 13 and the gripper piece 21 form an end effector 10, and in the end effector 10, the gripper piece 21 is openable and closable with respect to the treatment unit 13. Further, the end effector 10 and the rod member 6 are rotatable together with the shaft 3 and the rotation member 12 about the longitudinal axis C with respect to the housing 2. Meanwhile, it may be possible to fix the shaft 3, the end effector 10, and the rod member 6 to the housing 2 without arranging the rotation member 12.

Figure 2:
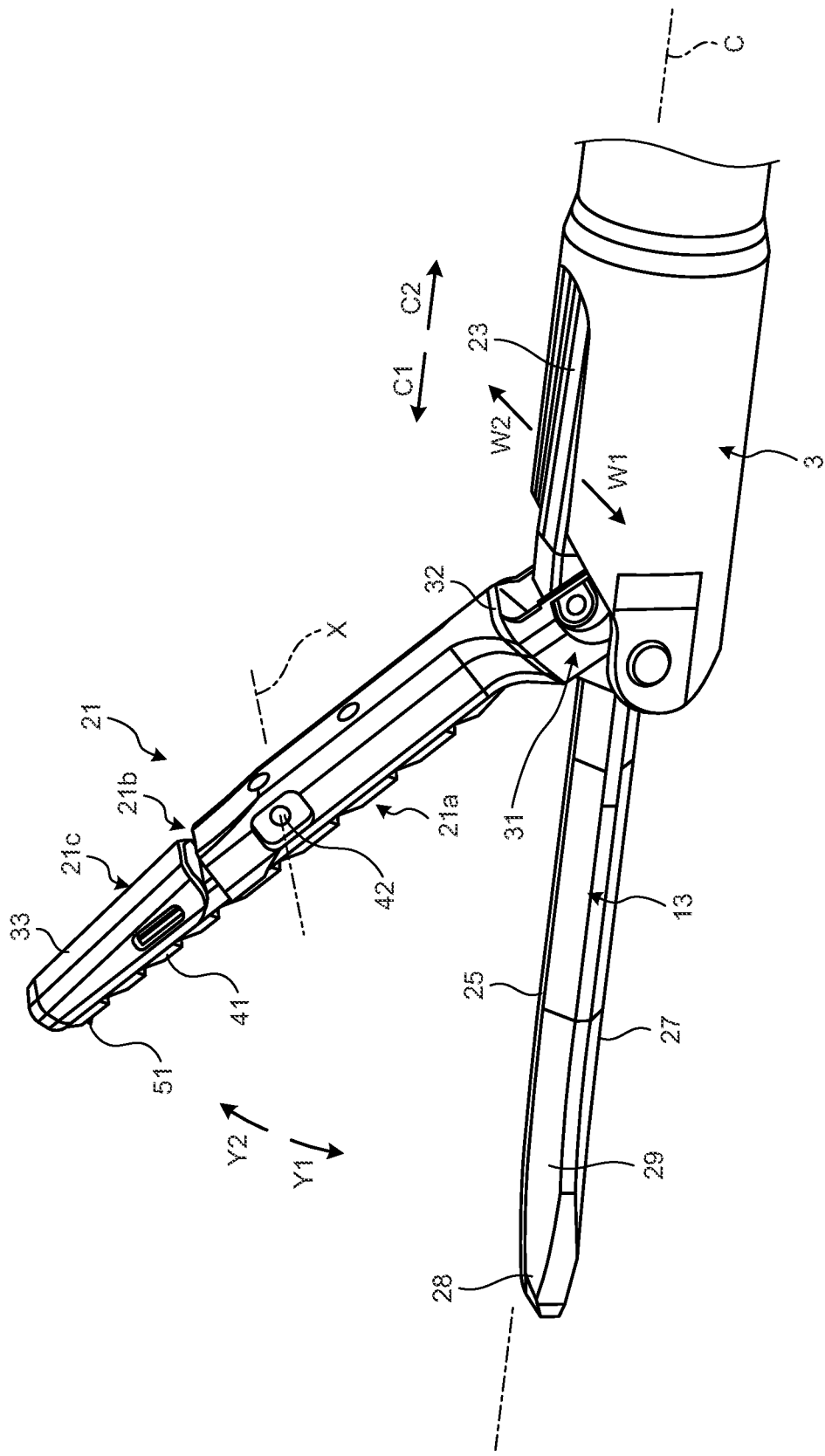
FIG. 2 is an enlarged view of a distal end portion of the exemplary treatment tool.
Figure 3:
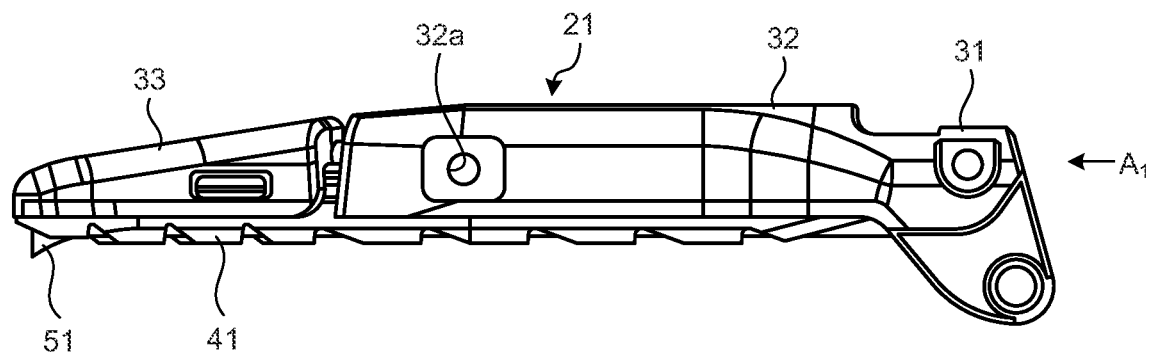
FIG. 3 is a diagram illustrating a configuration of a gripper piece included in the exemplary treatment tool.
Figure 4:
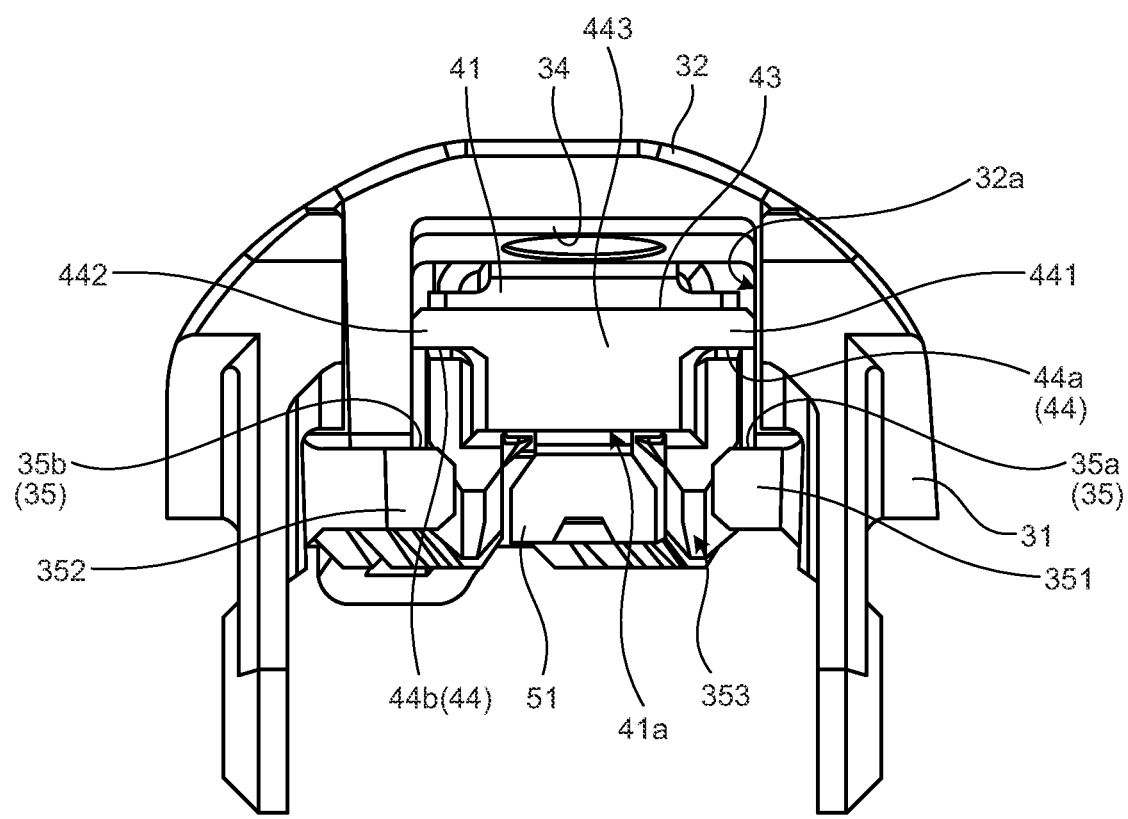
FIG. 4 is a plan view of the gripper piece viewed in a direction of an arrow A1 illustrated in FIG. 3.
Figure 5:
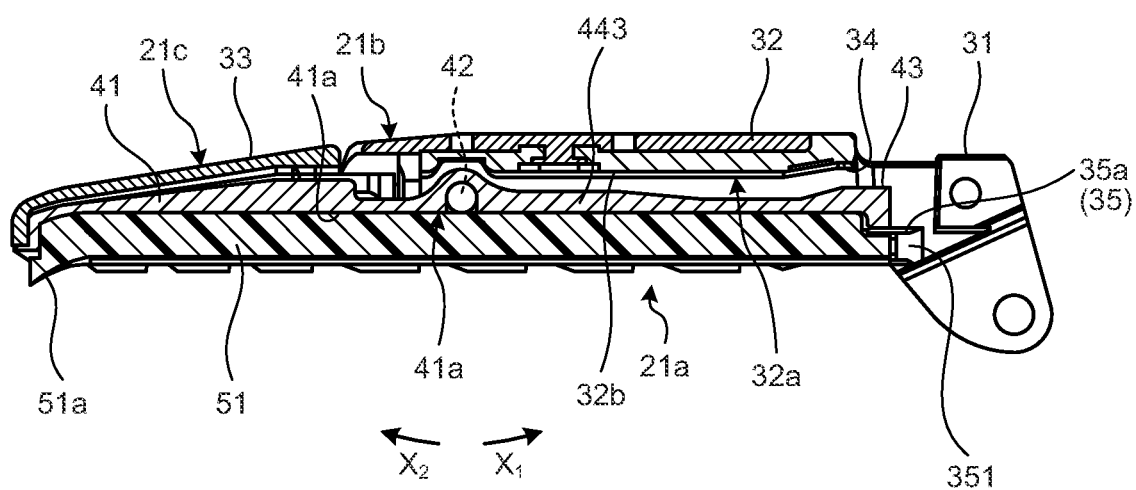
FIG. 5 is a cross-sectional view of the gripper piece illustrated in FIG. 3.

FIG. 2 is an enlarged view of a distal end portion of the treatment tool according to one embodiment of the disclosure. FIG. 3 is a diagram illustrating a configuration of the gripper piece included in the treatment tool according to one embodiment of the disclosure. FIG. 4 is a plan view of the gripper piece viewed in a direction of an arrow $A_1$ illustrated in FIG. 3. FIG. 5 is a cross-sectional view of the gripper piece illustrated in FIG. 3. FIG. 5 is a cross-sectional view cut along a plane that is parallel to the longitudinal axis C and that passes through the rod member 6 and the gripper piece 21. In the following, it is assumed that a direction that crosses (that is approximately perpendicular to) the longitudinal axis C and that crosses (that is approximately perpendicular to) the opening direction and the closing direction of the gripper piece 21 is referred to as a width direction (directions indicated by an arrow W1 and an arrow W2 illustrated in FIG. 2) of the end effector 10. FIG. 3 to FIG. 5 illustrate states in which a holder member 41 to be described later is arranged at a neutral position.

The treatment unit 13 includes a treatment surface (treatment unit facing surface) 25 that faces the gripper piece 21, and a back surface (treatment unit back surface) 27 that faces a side opposite to the treatment surface 25. A treatment unit inclined surface 28 that is inclined with respect to the longitudinal axis C is arranged on a distal end portion of the treatment surface 25. The treatment unit inclined surface (a rod side inclined surface) 28 is inclined so as to come closer to the back surface 27 side of the treatment unit 13 toward the distal end side. In the present embodiment, the treatment unit inclined surface 28 forms a distal end of the treatment surface 25 of the treatment unit 13, and is extended from the distal end of the treatment surface 25 to the proximal end side. Further, in the present embodiment, a bent extended portion (rod bending portion) 29 that is extended so as to bend with respect to the longitudinal axis C is arranged in the width direction of the end effector 10 on a distal end portion of the treatment unit 13. Furthermore, similarly to the treatment unit 13, the gripper piece 21 is arranged so as to bend with respect to the longitudinal axis C in the width direction of the end effector 10.

The gripper piece 21 includes a gripper surface (gripper piece facing surface) 21a that faces the treatment unit 13, and a back surface (gripper piece back surface) 21b that faces a side opposite to the gripper surface 21a. In the gripper piece 21, the gripper surface 21a is oriented to a side on which the gripper piece 21 is closed, and the back surface 21b is oriented to a side on which the gripper piece 21 is opened (side of the arrow Y2). Further, a bent extended portion (gripper piece bending portion) 21c that is extended so as to bend in the width direction of the end effector 10 with respect to the longitudinal direction (the longitudinal axis C) is arranged on a distal end portion of the gripper piece 21. The bent extended portion 21c of the gripper piece 21 bends in the width direction so as to face the bent extended portion 29 of the treatment unit 13.

The gripper piece 21 includes a jaw (movable jaw) 31 that is made of metal, for example. The jaw 31 is mounted on the shaft 3 in a rotatable manner. A proximal end portion of the jaw 31 is connected to the distal end portion of the movable member 23. The jaw 31 is extended from the proximal end portion to a central portion in the gripper piece 21.

Further, the gripper piece 21 includes a proximal end side cover 32 and a distal end side cover 33 that are made of resin. In the present embodiment, the jaw 31 is arranged in an integrated manner with the proximal end side cover 32. The jaw 31 and the proximal end side cover 32 are formed in an integrated manner by, for example, insert molding. The proximal end side cover 32 is firmly attached to a large part of an outer surface of the jaw 31. With the configuration as described above, in the back surface 21b of the gripper piece 21 or the like, the large part of the outer surface of the jaw 31 is not exposed to the outside of the gripper piece 21, and a large part of the back surface 21b of the gripper piece 21 is formed of the proximal end side cover 32 and the distal end side cover 33. Meanwhile, the proximal end side cover 32 may be configured as a member separated from the jaw 31, and the proximal end side cover 32 may be mounted on the outer surface of the jaw 31. Further, it may be possible to apply resin coating to the outer surface of the jaw 31, instead of firmly attaching the proximal end side cover 32 to the outer surface of the jaw 31. Here, materials of the proximal end side cover 32, the distal end side cover 33, and the coating are not limited to resin, but may be ceramics, rubber, or the like.

A concave portion 32a that is recessed to the side (direction of the arrow Y2) on which the gripper piece 21 is opened is formed on the jaw 31. The concave portion 32a is extended from a proximal end portion to a distal end portion of the proximal end side cover 32. The concave portion 32a passes through a central position of the gripper piece 21 in the width direction of the end effector 10. A distal end portion of the distal end side cover 33 forms the bent extended portion 21c of the gripper piece 21. Therefore, the distal end portion of the distal end side cover 33 is extended in the width direction of the end effector 10 so as to bend with respect to the longitudinal direction of the gripper piece 21.

The holder member 41 is mounted on the jaw 31. The holder member 41 is mounted on the jaw 31 with a support pin 42 illustrated in FIG. 2. The holder member 41 is made of, for example, metal, and is extended from the proximal end portion to the distal end portion in the gripper piece 21. An outer surface of the holder member 41 on the distal end side, in particular, an outer surface on the back surface 21b side, is covered with the distal end side cover 33. Further, the holder member 41 forms a part of the gripper surface 21a. Furthermore, a distal end portion of the holder member 41 forms the bent extended portion 21c of the gripper piece 21. Therefore, the distal end portion of the holder member 41 is extended in the width direction of the end effector 10 so as to bend with respect to the longitudinal direction of the gripper piece 21. Further, the holder member 41 is mounted on the jaw 31 in a manner of being inserted in concave portions of the proximal end side cover 32 and the distal end side cover 33 (or the jaw 31).

The holder member 41 swings with respect to the jaw 31 and the proximal end side cover 32 by using the support pin 42 as a central axis. The holder member 41 corresponds to a swinging member (swing arm). Further, the support pin 42 is extended in the width direction of the end effector 10.

Therefore, the holder member 41 swings with respect to the jaw 31 by using a swinging axis X extending in the width direction of the end effector 10 as the central axis. In this case, the distal end side cover 33 swings in conjunction with the holder member 41. Furthermore, the support pin 42 is located in the central portion of the gripper piece 21 in the longitudinal direction (the direction of the longitudinal axis C) of the gripper piece 21.

At the neutral position (see FIG. 3 to FIG. 5) at which the holder member 41 is extended approximately parallel to the jaw 31, the holder member 41 has a gap with respect to a concave portion (for example, a recessed bottom surface 32b (see FIG. 5) of the concave portion 32a) of the proximal end side cover 32 and the distal end side cover 33, and does not come into contact with the recessed bottom surface 32b.

Further, a length of a proximal end side (on the arrow C2 side) of the jaw 31 with reference to the support pin 42 as a base point is longer than a length of a distal end side (on the arrow C1 side) in the direction of the longitudinal axis C. Meanwhile, the proximal end side cover 32 has the same length relationship. Here, a length of a proximal end side of the holder member 41 with reference to the support pin 42 as a base point is approximately equal to a length of a distal end side in the direction of the longitudinal axis C. A fulcrum (the support pin 42) is located in the vicinity of the center, so that the holder member 41 is able to rotate smoothly.

Figure 6:
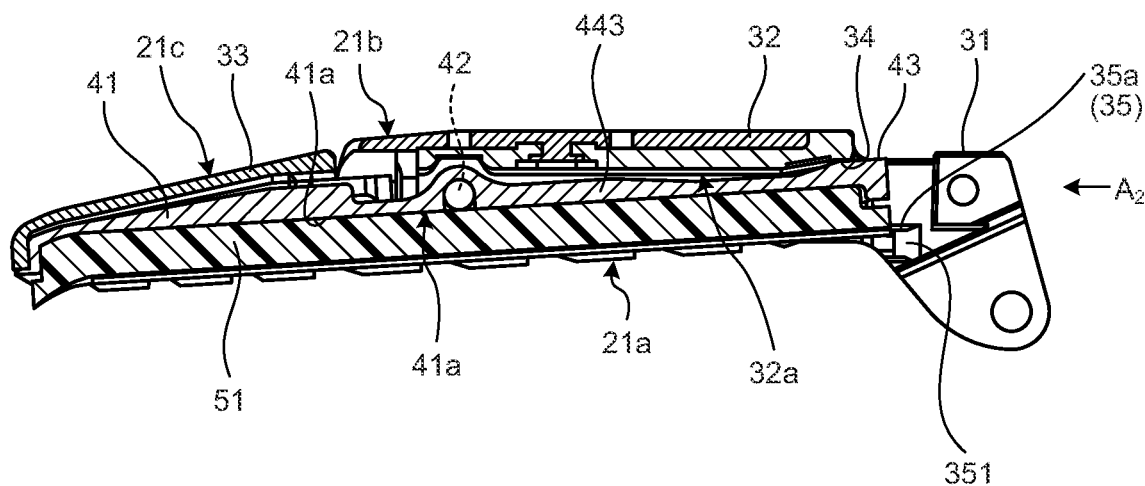
FIG. 6 is a diagram illustrating a configuration of the gripper piece included in the exemplary treatment tool, and is a diagram illustrating a state in which a swinging member is in a first regulated state.
Figure 7:
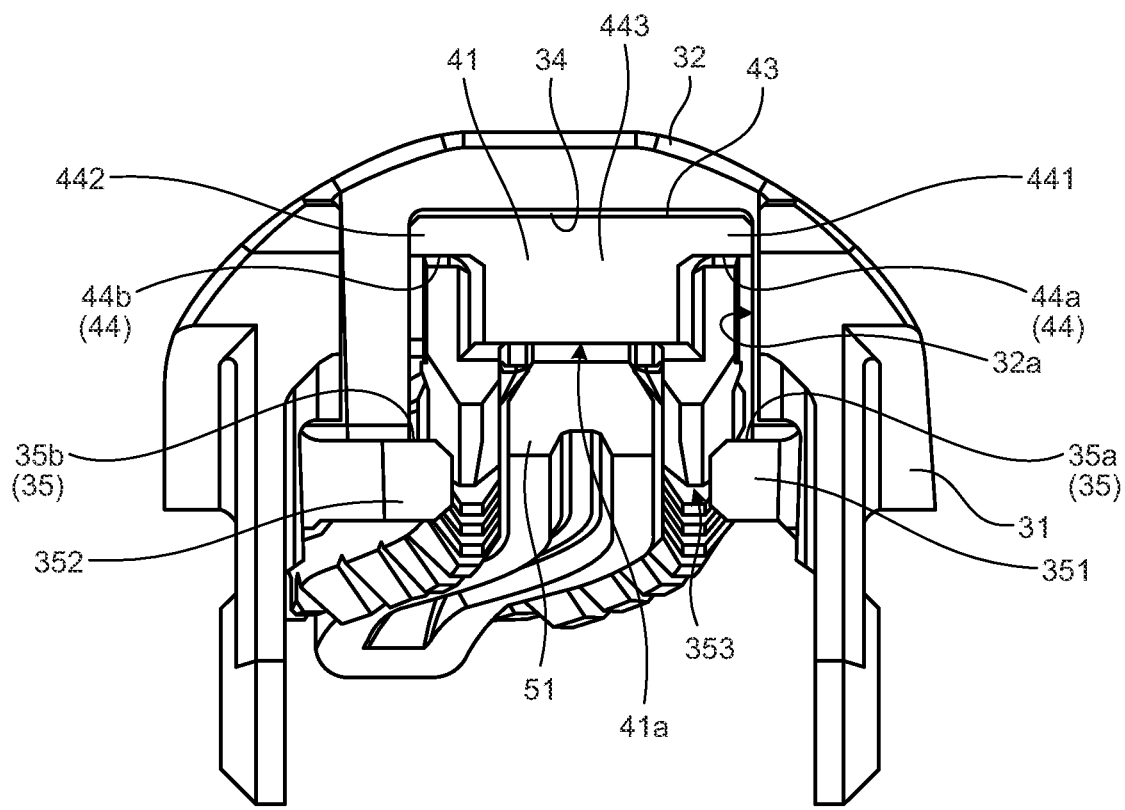
FIG. 7 is a plan view of the gripper piece viewed in a direction of an arrow A2 illustrated in FIG. 6.

FIG. 6 is a diagram illustrating a configuration of the gripper piece included in the treatment tool according to one embodiment of the disclosure, and is a diagram illustrating a case in which the swinging member is in a first regulated state. FIG. 7 is a plan view of the gripper piece viewed in a direction of an arrow $A_2$ illustrated in FIG. 6. FIGS. 6 and 7 are diagrams illustrating a case in which the holder member 41 swings in a direction of an arrow $X_1$ illustrated in FIG. 5.

Figure 8:
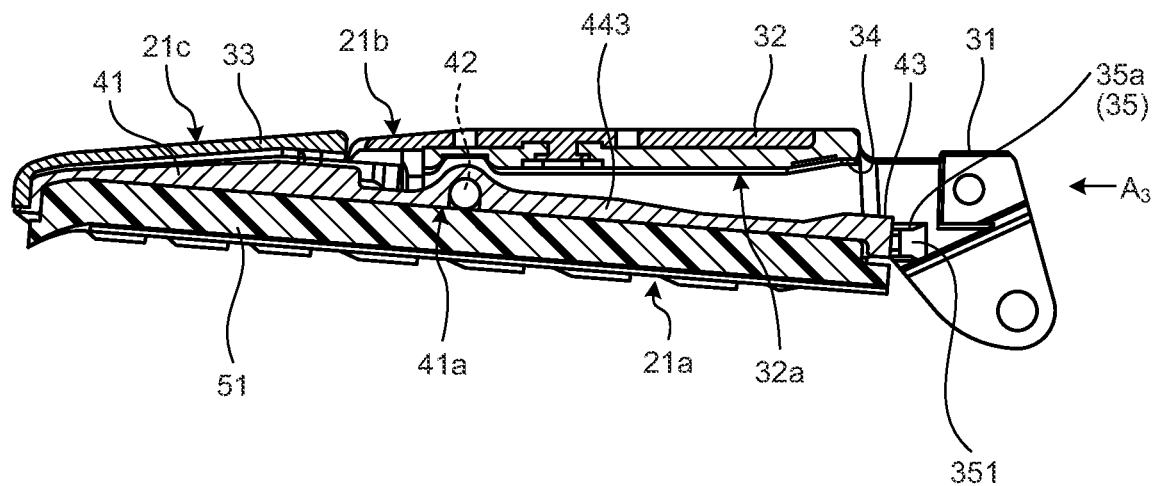
FIG. 8 is a diagram illustrating a configuration of the gripper piece included in the exemplary treatment tool, and is a diagram illustrating a state in which the swinging member is in a second regulated state.
Figure 9:
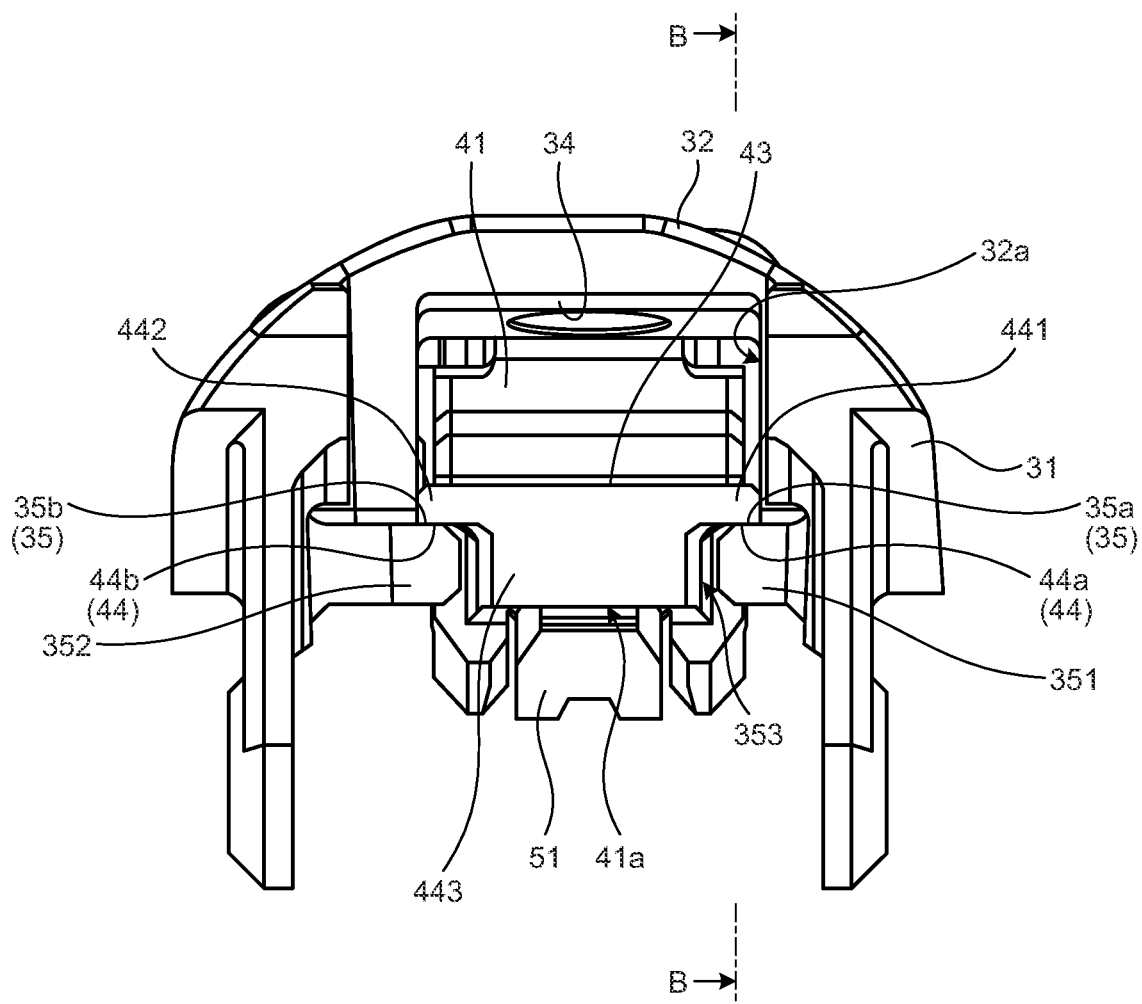
FIG. 9 is a plan view of the gripper piece viewed in a direction of an arrow A3 illustrated in FIG. 8.
Figure 10:
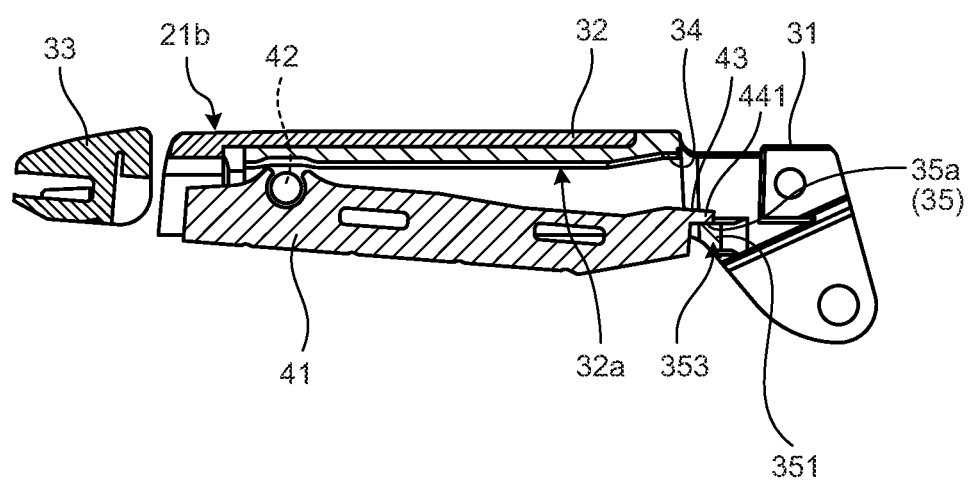
FIG. 10 is a cross-sectional view cut along a line B-B illustrated in FIG. 9.

FIG. 8 is a diagram illustrating a configuration of the gripper piece included in the treatment tool according to one embodiment of the disclosure, and is a diagram illustrating a case in which the swinging member is in a second regulated state. FIG. 9 is a plan view of the gripper piece viewed in a direction of an arrow $A_3$ illustrated in FIG. 8. FIG. 10 is a cross-sectional view cut along a line B-B illustrated in FIG. 9. FIGS. 8 to 10 are diagrams illustrating a case in which the holder member 41 swings in a direction of an arrow $X_2$ illustrated in FIG. 5.

If the holder member 41 swings from the neutral position to one side (the arrow $X_1$ side) in a swing direction, the holder member 41 comes close to the treatment unit 13 on the distal end side relative to the support pin 42. Then, in a region on the proximal end side relative to the support pin 42, a first contact surface 43 of the holder member 41 comes into contact with a first regulating surface 34 of the jaw 31 (see FIG. 6 and FIG. 7). In the state in which the first contact surface 43 comes into contact with the first regulating surface 34 (the first regulated state), swing of the holder member 41 to the one side in the swing direction is regulated.

In contrast, if the holder member 41 swings from the neutral position to the other side (the arrow $X_2$ side) in the swing direction, the holder member 41 comes close to the treatment unit 13 on the proximal end side relative to the support pin 42. Then, in a region on the proximal end side relative to the support pin 42, a second contact surface 44 of the holder member 41 comes into contact with a second regulating surface 35 of the jaw 31 (see FIG. 8 to FIG. 10). Here, the second regulating surface 35 is formed of two regulating surfaces (regulating surfaces 35a and 35b). The regulating surfaces 35a and 35b are respectively formed on two protruding portions (protruding portions 351 and 352) that protrude in mutually approaching directions inside the jaw 31. The regulating surfaces 35a and 35b correspond to upper surfaces of the projections that protrude in mutually approaching directions on an inner surface of the jaw 31. The second contact surface is formed of two contact surfaces (contact surfaces 44a and 44b) that are arranged at positions that come into contact with the two regulating surfaces (the regulating surfaces 35a and 35b). The contact surfaces 44a and 44b correspond to lower surfaces of projections 441 and 442 that protrude in a width direction on side surfaces of a proximal end portion of a main body 443 that constitutes a main body of the holder member 41. In a state in which the second contact surface 44 comes into contact with the second regulating surface 35 (second regulated state), swing of the holder member 41 to the other side in the swing direction is regulated.

Here, to prevent unnecessary interference with the projections 441 and 442, it is preferable that distal end portions of the protruding portions 351 and 352 are chamfered at least on sides that come into contact with the projections 441 and 442.

In the present embodiment, the first regulating surface 34 and the second regulating surface 35 that regulate the swing range of the holder member 41 are arranged on the proximal end side of the jaw 31. In addition, the first regulating surface 34 and the second regulating surface 35 are arranged on the proximal end side in the longitudinal direction of the gripper piece 21, and is arranged at positions separated from the support pin 42. By regulating swing of the holder member 41 at positions separated from the support pin 42, it is possible to reduce variation in swing (an angle with respect to the longitudinal axis C) due to variation in tolerance of each of the components of the gripper piece 21.

Further, the proximal end portion of the holder member 41 has a T-shape (see FIG. 4), and a part of the proximal end portion is inserted into a gap between the protruding portions 351 and 352 in a process of transition from the first regulated state to the second regulated state or in the reverse process. With the configuration in which a holder housing unit 353 is arranged such that a part of the holder member 41 is inserted into the gap between the protruding portions 351 and 352, it is possible to ensure an adequate stroke amount of the jaw 31 in a limited space.

Meanwhile, it is preferable to form a gap between each of the protruding portions 351 and 352 and the main body 443 to prevent unnecessary interference between each of the protruding portions 351 and 352 and the main body 443. The gap is, for example, equal to or larger than 0.05 millimeters (mm) and equal to or smaller than 0.5 mm. In this case, an extremely large gap prevents reduction in the size of the end effector 10.

Further, a pad member 51 is mounted on the holder member 41 (see FIG. 4 and FIG. 5). The pad member 51 forms a part of the gripper surface 21a of the gripper piece 21. The pad member 51 swings, together with the holder member 41, with respect to the jaw 31 by using the swinging axis X as a central axis. The pad member 51 is made of a resin material, such as polytetrafluoroethylene (PTFE). The pad member 51 is made of a material that prevents abrasion due to friction with the treatment unit 13 of the rod member 6 as much as possible, and that has heat resistance property. Furthermore, it is preferable that the pad member 51 has electrical insulating property.

A width of the pad member 51 is smaller than a distance between the protruding portions 351 and 352. Therefore, the pad member 51 is inserted into the gap between the protruding portions 351 and 352 (the holder housing unit 353) when, for example, the holder member 41 transitions from the first regulated state to the second regulated state. With the configuration in which the pad member 51 is inserted into the gap between the protruding portions 351 and 352, it is possible to ensure an adequate stroke amount of the jaw 31 in a limited space.

A distal end portion of the pad member 51 is an inclined surface 51a that is inclined with respect to the longitudinal direction of the gripper piece 21. The inclined surface 51a comes closer to the treatment unit 13 toward the distal end side. The treatment unit inclined surface 28 of the treatment unit 13 faces the pad member 51. Then, in a state in which a contact surface of the pad member 51 comes into contact with the treatment surface 25 of the treatment unit 13, the inclined surface 51a comes into contact with the treatment unit inclined surface 28. Meanwhile, it is preferable that the inclined surface 51a is approximately parallel to the treatment unit inclined surface 28 in the state in which the pad member 51 comes into contact with the treatment unit 13. Furthermore, the inclined surface 51a protrudes to the treatment unit 13 side relative to a region other than the inclined surface 51a on the contact surface of the pad member 51.

The holder member 41 includes a concave portion 41a that is recessed to a side on which the gripper piece 21 is opened. The concave portion 41a is extended from the proximal end portion to the distal end portion of the gripper piece 21. In the present embodiment, the distal end portion of the holder member 41 is extended so as to bend with respect to the longitudinal direction of the gripper piece 21, so that a distal end portion of the concave portion 41a is also extended so as to bend with respect to the longitudinal direction of the gripper piece 21. Furthermore, the concave portion 41a passes through a central position in the width direction of the end effector 10. The pad member 51 is fixed to the holder member 41 in a state of being inserted in the concave portion 41a. The pad member 51 is fixed to the holder member 41 by locking, bonding, or the like.

Here, to prevent backlash, it is desirable to arrange the regulating surfaces at positions that are separated from the support pin 42 as much as possible. However, if the regulating surfaces are to be arranged on the distal end side of the holder member 41, a size of a distal end portion of the end effector 10 increases. To perform fine treatment, it is preferable to reduce the size of the distal end of the end effector 10.

According to the embodiment as described above, the first regulating surface 34 and the second regulating surface 35 arranged on the proximal end side of the gripper piece 21 regulate swing of the holder member 41. Further, in the present embodiment, the first regulating surface 34 and the second regulating surface 35 are arranged at certain positions separated from the support pin 42 that serves as the central axis of the swing of the holder member 41, that is, at certain positions that come into contact with the contact surfaces (the first contact surface 43 and the second contact surface 44) arranged on the proximal end portion of the holder member 41. According to the present embodiment, by regulating the swing range of the holder member 41 on the proximal end side of the gripper piece 21, it is possible to arrange the first regulating surface 34 and the second regulating surface 35 at certain positions separated from the support pin 42, and it is possible to prevent backlash of the holder member 41 (swinging member).

Furthermore, in the embodiment as described above, the length of the proximal end side (the arrow C2 side) of the jaw 31 in the longitudinal axis C with use of the support pin 42 as a base point is set to be longer than the length of the distal end side (the arrow C1 side), so that it is possible to reduce the size of the end effector 10, in particular, reduce the size of the distal end portion.

In contrast, in a configuration in which regulating units for the rotation range of the jaw are arranged on both of the distal end side and the proximal end side and the length of the distal end side in the longitudinal axis direction with use of a rotation axis as a base point is shorter, it is difficult to ensure accuracy of regulation positions and a rotation width is likely to vary. Furthermore, if the length of the distal end side of the jaw is increased, it is possible to ensure the accuracy of the regulation positions, but the size of the distal end portion increases. Therefore, by adopting the configuration in which the regulating units are arranged on only the proximal end side of the jaw 31 as in the present embodiment, it is possible to ensure the accuracy and prevent an increase in the size of the distal end portion.

While the embodiment of the disclosure has been explained above, the disclosure is not limited to only the embodiment as described above. The disclosure may include various embodiments and the like that are not described herein. In the embodiment as described above, the treatment tool 1 is configured to apply ultrasound vibration to living tissue, but the disclosure is not limited to this example, and it may be possible to adopt a configuration in which high-frequency energy or thermal energy is applied in addition to ultrasound vibration, or it may be possible to adopt a configuration in which ultrasound vibration, high-frequency energy, and thermal energy can selectively be applied.

Figure 11:
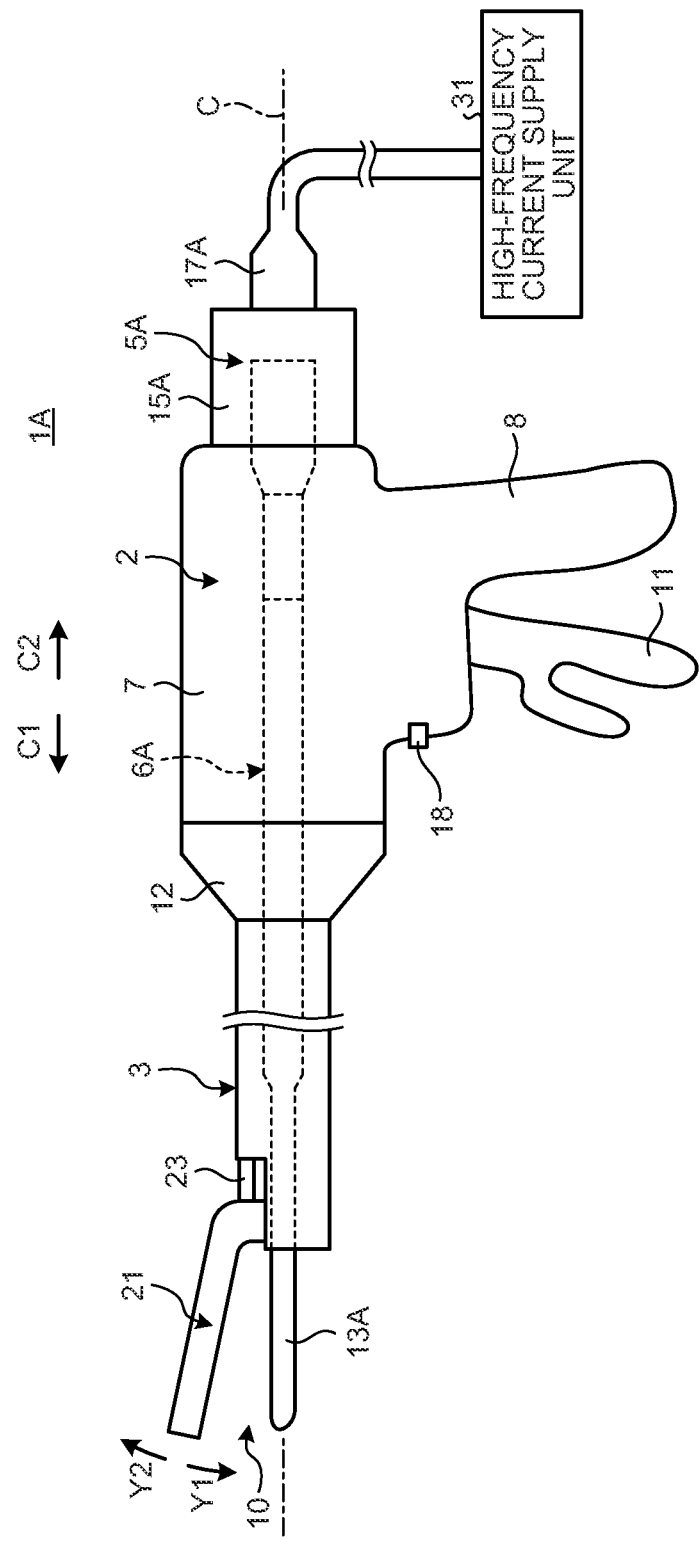
FIG. 11 is a schematic diagram illustrating an exemplary treatment tool.

FIG. 11 is a schematic diagram illustrating another exemplary treatment tool. For example, in a case of a configuration in which high-frequency energy is applied, a high-frequency generation unit 5A and a rod member 6A are arranged instead of the transducer unit 5 and the rod member 6, and high-frequency electric current is transmitted as high-frequency energy to the rod member 6A. Specifically, a treatment tool 1A includes the housing 2, the shaft 3, the high-frequency generation unit 5A, and the rod member (probe) 6A. The high-frequency generation unit 5A includes a case 15A. The case 15A is mounted on the housing main body 7 from the proximal end side. Further, one end of a cable 17A is connected to the case 15A. The other end of the cable 17A is removably connected to a high-frequency electric current supply unit 31 that supplies electrical energy. In this case, a lead wire (not illustrated) is arranged between the cable 17A and the rod member 6A and between the cable 17A and the housing main body 7, so that the high-frequency electric current flows into a treatment unit 13A on a distal end of the rod member 6A and the holder member 41. The treatment unit 13A and the holder member 41 function as a pair of electrodes that establish conduction of the high-frequency electric current. In the treatment tool 1A, a treatment target is treated by causing the high-frequency electric current to flow into the treatment unit 13A and the holder member 41.

According to the disclosure, it is possible to prevent an increase in a size of an end effector and prevent backlash of a swinging member that is arranged on a distal end.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool comprising:
   an elongated shaft;
   a probe that protrudes from a distal end of the shaft;
   a movable jaw that is mounted in the treatment tool in a rotatable manner; and
   a swing arm that is pivotably mounted on the movable jaw, the swing arm being configured to grip living tissue with the probe and swing with respect to the movable jaw, wherein:
   the movable jaw includes:
      a first regulating surface that is configured to contact a first contact region in a proximal end portion of the swing arm to regulate swinging of the swing arm in a first direction, and
      a second regulating surface that is configured to contact a second contact region in the proximal end portion of the swing arm to regulate swinging of the swing arm in a second direction, the first contact region being different from the second contact region, the second regulating surface being formed on two protruding portions that are arranged inside the movable jaw and that protrude in mutually approaching directions,
   the proximal end portion of the swing arm includes a projection that protrudes in a direction that is perpendicular to: (i) a longitudinal direction of the swing arm and (ii) a swing direction of the swing arm,
   the projection is configured to contact the second regulating surface, and
   a part of the proximal end portion of the swing arm is configured to be inserted between the two protruding portions of the movable jaw in a state in which the projection contacts the second regulating surface.

2. The treatment tool according to claim 1, wherein the swing arm is configured to swing with respect to the movable jaw about a fulcrum that is spaced in a distal direction from the first regulating surface, the second regulating surface, the first contact region, and the second contact region.

3. The treatment tool according to claim 2, wherein a length of a proximal portion of the movable jaw extending in a proximal direction from the fulcrum to a proximal end of the jaw is longer than a length of a distal portion of the jaw extending in the proximal direction from a distal end of the jaw to the fulcrum.

4. The treatment tool according to claim 3, wherein a length of a proximal portion of the swing arm extending in the proximal direction from the fulcrum to a proximal end of the swing arm is approximately equal to a length of a distal portion of the swing arm extending in the proximal direction from a distal end of the swing arm to the fulcrum.

5. The treatment tool according to claim 2, wherein the fulcrum is a support pin, and the swing arm is pivotably mounted to the jaw with the support pin.

6. The treatment tool according to claim 1, wherein the swing arm includes a pad member that is configured to contact the probe when the movable jaw is rotated to a closed position with respect to the probe.

7. The treatment tool according to claim 1, wherein the probe, the swing arm, and the movable jaw are each bent with respect to a longitudinal direction of the shaft.

8. The treatment tool according to claim 6, wherein the pad member extends to a proximal end of the swing arm.

9. The treatment tool according to claim 1, further comprising:
   an ultrasound transducer configured to generate ultrasound vibration,
   wherein the probe is configured to vibrate in a longitudinal direction of the shaft due to the ultrasound vibration generated by the ultrasound transducer.

10. The treatment tool according to claim 1, wherein:
    the probe is configured to receive a high-frequency electric current, and
    the probe and the swing arm form a pair of electrodes that are configured to establish conduction of the high-frequency electric current.

11. The treatment tool according to claim 1, the swing arm is configured to:
    swing in the first direction such that a distal end of the swing arm moves closer to the probe and a proximal end of the swing arm moves away from the probe, and
    swing in the second direction such that the distal end of the swing arm moves away from the probe, and the proximal end of the swing arm moves closer to the probe.

12. The treatment tool according to claim 1, wherein the swing arm includes a concave portion that is recessed in a direction away from the probe, and a pad member is inserted in the concave portion and is fixed to the swing arm.

13. The treatment tool according to claim 1, wherein the movable jaw is configured to rotate so as to open and close with respect to the probe.

14. The treatment tool according to claim 1, wherein the movable jaw is rotatably mounted on the shaft.

15. A treatment tool comprising:
    an elongated shaft;
    a probe that protrudes from a distal end of the shaft;
    a movable jaw that is mounted in the treatment tool in a rotatable manner; and
    a swing arm that is pivotably mounted on the movable jaw, the swing arm being configured to grip living tissue with the probe and swing with respect to the movable jaw, wherein:
    the movable jaw includes:
       a first regulating surface that is configured to contact a first contact region in a proximal end portion of the swing arm to regulate swinging of the swing arm in a first direction, and
       a second regulating surface that is configured to contact a second contact region in the proximal end portion of the swing arm to regulate swinging of the swing arm in a second direction, the first contact region being different from the second contact region, the second regulating surface being formed on two protruding portions that are arranged inside the movable jaw and that protrude in mutually approaching directions,
    the swing arm includes a pad member that is configured to contact the probe when the movable jaw is rotated to a closed position with respect to the probe, and
    a width of the pad member is smaller than a distance between the two protruding portions of the movable jaw.

\* \* \* \* \*